United States Patent [19]

Aucutt

[11] Patent Number: 5,238,846
[45] Date of Patent: Aug. 24, 1993

[54] METHOD OF DETECTING THE PRESENCE OF SUGAR IN STEAM GENERATING SYSTEMS

[75] Inventor: Michael J. Aucutt, Cedar Rapids, Iowa

[73] Assignee: Betz Laboratories, Inc., Trevose, Pa.

[21] Appl. No.: 853,638

[22] Filed: Mar. 18, 1992

[51] Int. Cl.$^5$ ............................................ G01N 31/00
[52] U.S. Cl. ...................................... 436/38; 436/95; 436/164; 436/805
[58] Field of Search .................... 436/38, 164, 95, 805

[56] References Cited

U.S. PATENT DOCUMENTS

| 2,608,533 | 8/1952 | Carson et al. | 436/95 |
| 2,659,700 | 11/1953 | Carson et al. | 436/95 |
| 4,608,345 | 8/1986 | Feldman et al. | 436/60 |
| 4,617,278 | 10/1986 | Reed | 436/60 |

*Primary Examiner*—Lyle A. Alexander
*Attorney, Agent, or Firm*—Alexander D. Ricci; Gregory M. Hill

[57] ABSTRACT

A method for detecting the presence of sugars in the water of a steam generating system by using an indicator composition comprised of potassium permanganate and an acetate in an aqueous solution. After a period of time, depending upon the temperature of the sample tested, the color of the sample is observed to determine if sugars are present in the water.

8 Claims, No Drawings

METHOD OF DETECTING THE PRESENCE OF SUGAR IN STEAM GENERATING SYSTEMS FIELD OF THE INVENTION

The present invention relates to steam generating systems such as boilers. Specifically, the invention is directed toward a method of detecting the presence of sugars in the water used to generate steam in such systems.

BACKGROUND OF THE INVENTION

In steam generating systems, such as boilers, the condensate feedwater may contain a variety of contaminants which will contribute to inefficiencies in the operation of the system. Under steam generating conditions, some compounds will detrimentally affect the heat transfer characteristics of the entire system. This results in undesirable downtime to make costly repairs.

Acids are especially corrosive. They may be generated from a number of precursors which are present in the feedwater introduced into the system. Under the elevated temperature conditions necessary to generate steam, these precursors will become acidified. Sugars, such as glucose and fructose, are such precursors. When these sugars are oxidized, they will form various organic acids. These acids, then, will be available to corrosively attack the internal metallic surfaces of the entire steam generating system.

It is most desirable, therefore, to eliminate or neutralize the acidic species in the condensate feedwater. It is even more desirable, however, to eliminate the precursor from the feedwater before it turns acidic. In order to do this, the presence of the precursor must first be detected.

In condensate feedwater which may contain carbohydrates, it is very important to be able to detect the presence of these "sugars" as soon as they enter the feedwater train and at the lowest concentration possible. Conventional analysis methods for detecting the presence of sugars in aqueous systems include the use of Fehlings solution, Benedicts solution (copper is reduced by the sugars present) or by glucose enzymatic test strips (available from Lilly as TES-TAPE ®). Unfortunately, these methods are limited in their detection limits. For example, enzyme test strips fail to successfully detect the presence of sugars at concentrations of lower than 0.05% or 500 ppm. The high concentration detection minimum limit renders such methods useless where sugar concentrations are below this value but still high enough to generate corrosion causing acids.

Additionally, the use of test methods such as Benedicts or Fehlings, requires that the solution be heated to boiling. The temperature limitation mitigates against the use of such methods to analyze higher temperature condensate streams. Furthermore, these tests are not quantitative and render photometric analysis ineffectual because of the precipitate that forms. It is an object of the present invention to provide a method for quantitatively detecting the presence of sugars in steam generating system feedwaters at very low concentrations. It is a further object to provide a method for detecting the presence of low concentrations of sugars in high temperature condensate streams on an on-line basis.

DETAILED DESCRIPTION OF THE INVENTION

The present invention consists of a method for detecting the presence of sugars, such as glucose, and fructose, in the water of steam generating systems. This method utilizes an indicator comprised of alkaline potassium permanganate ($KMnO_4$) complexed with an acetate.

In nonenzymatic oxidations of carbohydrates, aldoses, react as do aldehydes, oxidization occurs at the C—HO group, oxidization can also proceed to break the carbon to carbon bonds.

$$RCHO \rightarrow Oxidation \rightarrow RCOOH$$

Potassium permanganate is a powerful oxidizing agent either in an acidic or basic medium, as shown below by its standard electrode potential at 25° C.

Acidic: $MnO_4^{-2}$ (ag)+$8H^+$ (ag) +$5e^- \rightarrow Mn^2$ (ag) +$4H_2O$ (l) $E^o(v)+1.51$ Basic: $MnO_4^{-2}$ (ag)+$2H_2O$(l)+$3e^- \rightarrow MnO_2 + 4OH^-$(ag) $E^o(V)+0.45$ Potassium permanganate has widely and commonly been used in organic oxidization, and will readily oxidize the aldehyde group of carbohydrates. In the process, manganese is reduced from the +7 to the +2 oxidization state. Permanganate is a colored anion and reduction is visually observable from purple to pink brown.

The indicator of the present invention is formulated by dissolving $KMnO_4$, sodium acetate and sodium hydroxide into organic free water. The various ingredients of the indicator may be combined in the following amounts:

0.25 to 2.5 grams potassium permanganate
0.25 to 1.5 grams sodium acetate
5 ml to 15 ml 1N sodium hydroxide
remainder to 100 ml to 200 ml organic free water The following formulation has been found to be highly effective in the field and is preferred for achieving the stated objectives of the invention.

FORMULATION 1

2.5 grams potassium permanganate
1.5 grams sodium acetate
15 ml 1N sodium hydroxide
Remainder organic free water to 200 ml It was discovered that the mixture of alkaline permanganate/acetate will generate specific color changes, other than permanganate alone, with carbohydrates, aldehydes and organic compounds containing the R-CHO group.

The "Baeyer Test" was used for years to detect unsaturation.

$$CH=CH \xrightarrow{KMnO_4} \underset{OH\ \ OH}{-C-C-} + MnO_2$$

Purple           Pink Brown

However, as indicated previously the color response was limited.

The alkaline $MnO_4$/acetate mixture gives a broader color range dependent upon concentration.

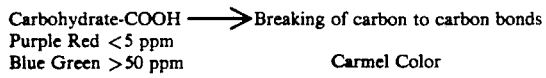

The water to be tested may be removed from the steam generating system at any convenient location. However, it is most desirable to test for sugar contamination in the water entering the system as feedwater. This way, if sugars are detected at an early stage before they have had a chance to lower the pH throughout the entire system, corrective measures can be taken to alleviate corrosive damage to system equipment.

Since the MnO4/acetate indicator changes color in the presence of sugars, the indicator will react as follows:

| 0 Carbohydrates | Purple (Blank) |
| 1 to 25 ppm at 90C | Purple Red |
| 25 to 50 ppm at 90C | Violet Blue |
| 50 ppm to 100 ppm at 25C | Blue Green to *carmel |

*At elevated temps and time oxidization will proceed to breakage of carbon to carbon bonds at which point the indicator will eventually turn carmel color.

The above reaction times are from 30 seconds to one minute.

Observations are best made by placing the water to be tested into a suitable transparent container, such as a test tube. The indicator is then added dropwise into the container. The amount of indicator may vary from about 0.01 ml to 2 ml and the size of the sample of water may be in the range of 0.05 to 100 ml. The most desirable ratio, by volume of indicator to sample water has been found to be about 1 to 50.

In another mode of operation, sugar concentration may be monitored on a continuous or periodic on-line basis. Water may be automatically drawn off at some point of the steam generating system, such a the condensate stream and fed to a device for photometric analysis of the water sample. The device must be capable of making color comparisons between a treated sample and a previously calibrated color standard. An example of such a device is a photometric analyzer, such as of the types commercially available from the Mach Company.

If the analyzer device is set up near the condensate stream, a sample of the high temperature condensate is drawn off and deposited into a sample cell in the device. The indicator is added to the sample cell and after a predetermined period of time, usually about 30 seconds, the photometric cell measures the percent transmission of the sample and compares it to the pre-calibrated color standard to determine the amount of sugar present in the sample. The device can be programmed to set off an alarm if the concentration of sugar exceeds a certain value, such as, for example 1 ppm.

In order to effectively utilize an on-line analyzing device, it is essential that pre-calibrated color standards as a function of known concentration of suspected contaminants be established. For example, if fructose was known to be a potential periodic contaminant, a concentration/color standard curve would need to be generated by the user employing the indicator of Formulation I.

EXAMPLES

In order to exhibit the efficacy of the indicator according to the present invention, the following tests were performed. Individual water samples were prepared each having different concentrations of contaminants. The sugar used was a combination of fructose and glucose. Aldehydes were tested in order to show the ability of the present indicator to differentiate between simple aldehydes and sugars. Acetaldehyde and formaldehyde were used as the aldehydes.

A 25 ml sample of water containing each of the various concentrations of the contaminants indicated was placed into a test tube. One-half ml of the indicator of Formulation I was then added and the color change exhibited after the time indicated was recorded. Samples were prepared at both room temperature (25° C.) and at typical condensate stream temperatures (180°–193° F.).

TABLE I

Reactions of Indicator with Carbohydrates (Fructose) at high ranges, at 25° C.

| mg/L | Reaction Time | Color | Temp |
| --- | --- | --- | --- |
| 500 ppm | 30 Seconds | Blue Green | 25° C. |
| 400 | 30 Seconds | Blue Green | 25° C. |
| 300 | 30 Seconds | Blue Green | 25° C. |
| 100 | 30 Seconds | Blue Green | 25° C. |
| 50 | No Reaction | Purple | 25° C. |

TABLE II

Reactions of Indicator with Carbohydrates (Fructose) at low ranges and elevated temps: 90° C.

| mg/L | Reaction Time | Color |
| --- | --- | --- |
| 50 ppm | One Minute | Blue Green to Carmel |
| 25 ppm | One Minute | Violet Red to Carmel |
| 15 ppm | One Minute | Purple Red |
| 5 ppm | One Minute | Purple Red |
| 2 ppm | One Minute | Purple Red |

TABLE III

Reactions of Indicator with other Organic and Inorganic Materials

| Compound mg/L | Reaction Time | Color Range | Temp |
| --- | --- | --- | --- |
| Ethyl Alcohol 20 ppm | One Minute | Brown | 80° C. |
| Acetone | No Reaction | — | 90° C. |
| Formaldehyde 20 ppm | One Minute | Pink Yellow | 90° C. |
| Formaldehyde 100 ppm | Two Seconds | Pink | 25° C. |
| FeSO4 10 ppm | One Minute | Red | 90° C. |
| Cyclohexanone 50 ppm | One Minute | Green | 25° C. |
| Acetic Acid 50 ppm | No Reaction | — | 90° C. |
| Corn Oil 20 ppm | One Minute | Red | 90° C. |

The permanganate/acetate indicator of the present invention has detected carbohydrate leaks in condensate streams from heat exchangers at several grain processing plants in the midwest. These leaks were confirmed when concentrations reached 500 ppm and were picked up by glucose Tes-Tape ®. Corrective action was therefore able to be performed at an earlier stage than would otherwise have been possible using the conventional Tes-Tape ®.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What I claim is:

1. A method for the detection of a sugar at a concentration of less than 500 ppm in the water of a steam generating system, which comprises;

obtaining a sample of water from the system;

mixing the sample with an indicator which comprises potassium permanganate, sodium hydroxide and sodium acetate to form an aqueous reaction mixture;

correlating a change in the color of the reaction mixture to a concentration of sugar in the sample.

2. The method of claim 12 wherein the steam generating system is a boiler system.

3. The method of claim 1 wherein the water is the feedwater.

4. The method of claim 1 wherein the color is observed after 30 seconds when the water sample is tested at or about room temperature.

5. The method of claim 1 wherein the color is observed after 20 seconds when the water sample is tested at elevated temperatures.

6. The method of claim 1 wherein the ratio, by volume, of the indicator to a sample of the water is about 1 to 50.

7. The method of claim 1 wherein the indicator comprises from about 0.25 to 2.5 grams potassium permanganate, from about 0.25 to 1.5 grams sodium acetate, from about 5 ml to 15 ml 1N sodium hydroxide and the remainder organic free water to from 100 ml to 200 ml.

8. The method of claim 7 wherein the indicator comprises approximately 2.5 grams potassium permanganate, 1.5 grams sodium acetate, 15 ml 1N sodium hydroxide and remainder organic free water to 200 ml.

* * * * *